United States Patent
Hu et al.

(10) Patent No.: US 10,811,141 B2
(45) Date of Patent: Oct. 20, 2020

(54) RECOGNIZING PREDICTIVE PATTERNS IN THE SEQUENCE OF SUPERALARM TRIGGERS FOR PREDICTING PATIENT DETERIORATION

(71) Applicant: THE REGENTS OF THE UNIVERSITY OF CALIFORNIA, Oakland, CA (US)

(72) Inventors: Xiao Hu, San Francisco, CA (US); Yong Bai, San Francisco, CA (US); Rebeca Salas-Boni, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1002 days.

(21) Appl. No.: 15/332,784

(22) Filed: Oct. 24, 2016

(65) Prior Publication Data

US 2017/0046499 A1 Feb. 16, 2017

Related U.S. Application Data

(63) Continuation of application No. PCT/US2015/027839, filed on Apr. 27, 2015.
(Continued)

(51) Int. Cl.
*G16H 50/50* (2018.01)
*G16H 50/70* (2018.01)
(Continued)

(52) U.S. Cl.
CPC ............ *G16H 50/50* (2018.01); *A61B 5/00* (2013.01); *A61B 5/746* (2013.01);
(Continued)

(58) Field of Classification Search
CPC ........ G16H 50/50; G16H 50/20; G16H 50/70; G06F 19/00; G06F 16/2465; G06F 16/252; G06Q 50/24; A61B 5/746; A61B 5/00
See application file for complete search history.

(56) References Cited

U.S. PATENT DOCUMENTS

5,319,355 A * 6/1994 Russek ............... A61B 5/0002
340/573.1
7,225,013 B2 5/2007 Geva et al.
(Continued)

FOREIGN PATENT DOCUMENTS

WO 2013-056180 A1 4/2013

OTHER PUBLICATIONS

Hu, Xiao et. Al. "Predictive combinations of monitor alarms preceding in-hospital code blue events." Journal of Biomedical Informatics. 45 (2012) pp. 913-912 (Year: 2012).*
(Continued)

*Primary Examiner* — Linh Giang Le
(74) *Attorney, Agent, or Firm* — O'Banion & Ritchey LLP; John P. O'Banion

(57) ABSTRACT

Methods for predicting patient deterioration or clinical events by detecting patterns in heterogeneous temporal clinical data streams that are predictive of certain clinical end points and matching the patient state with those patterns are described. The detected patterns, referred to as SuperAlarm triggers, are a predictive combination of frequently co-occurring monitor alarms, conditions and laboratory test results that can predict patient deterioration for imminent life-threatening events. SuperAlarm triggers may also exhibit patterns in the sequence of SuperAlarms that are triggered over the monitoring time of a patient. Sequential patterns of SuperAlarm triggers may also indicate a temporal process of change in patient status. SuperAlarm based alerts will also greatly reduce the number of false alarms and alarm fatigue compared to conventional alarms.

23 Claims, 1 Drawing Sheet

Related U.S. Application Data

(60) Provisional application No. 62/137,342, filed on Mar. 24, 2015, provisional application No. 61/984,172, filed on Apr. 25, 2014, provisional application No. 61/984,162, filed on Apr. 25, 2014.

(51) Int. Cl.

| | |
|---|---|
| *G16H 50/20* | (2018.01) |
| *G06F 16/25* | (2019.01) |
| *G06F 16/2458* | (2019.01) |
| *A61B 5/00* | (2006.01) |
| *G06Q 50/24* | (2012.01) |
| *G06F 19/00* | (2018.01) |

(52) U.S. Cl.
CPC ........ *G06F 16/2465* (2019.01); *G06F 16/252* (2019.01); *G06F 19/00* (2013.01); *G06Q 50/24* (2013.01); *G16H 50/20* (2018.01); *G16H 50/70* (2018.01)

(56) References Cited

U.S. PATENT DOCUMENTS

| | | | |
|---|---|---|---|
| 7,949,186 B2* | 5/2011 | Grauman | G06K 9/4671 |
| | | | 382/159 |
| 2011/0191270 A1 | 8/2011 | Peng et al. | |
| 2012/0122432 A1 | 5/2012 | Bellomo et al. | |
| 2013/0080425 A1* | 3/2013 | Kwete | G16H 10/60 |
| | | | 707/723 |

OTHER PUBLICATIONS

Burdick, Doug et. Al. "MAFIA: A Maximal Frequent Itemset Algorithm for Transactional Databases." IEEE 2001: pp. 443-452 (Year: 2001).*

Korean Intellectual Property Office (KIPO), International Search Report and Written Opinion, dated Aug. 7, 2015, related PCT International Application No. PCT/US2015/027839, pp. 1-15, with claims searched, pp. 16-22.

* cited by examiner

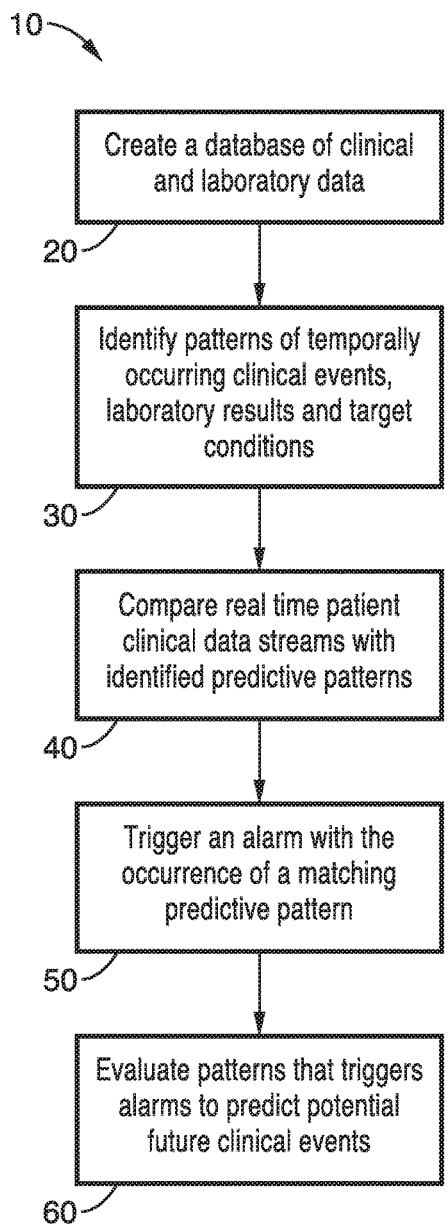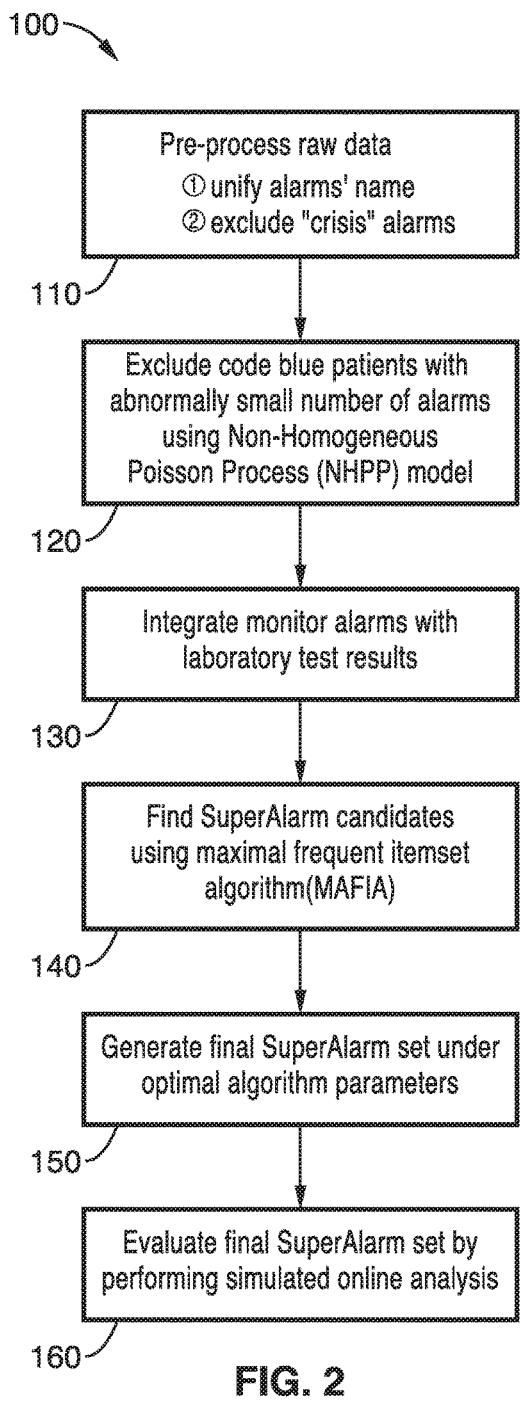

RECOGNIZING PREDICTIVE PATTERNS IN THE SEQUENCE OF SUPERALARM TRIGGERS FOR PREDICTING PATIENT DETERIORATION

CROSS-REFERENCE TO RELATED APPLICATIONS

This application is a 35 U.S.C. § 111(a) continuation of PCT international application number PCT/US2015/027839 filed on Apr. 27, 2015, incorporated herein by reference in its entirety, which claims priority to, and the benefit of, U.S. provisional patent application Ser. No. 62/137,342 filed on Mar. 24, 2015, incorporated herein by reference in its entirety, and from U.S. provisional patent application Ser. No. 61/984,162 filed on Apr. 25, 2014, incorporated herein by reference in its entirety, and from U.S. provisional patent application Ser. No. 61/984,172 filed on Apr. 25, 2014, incorporated herein by reference in its entirety. Priority is claimed to each of the foregoing applications.

The above-referenced PCT international application was published as PCT International Publication No. WO 2015/164879 on Oct. 29, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The present technology pertains generally to patient monitoring systems and more particularly to methods for identifying and differentiating patterns in sequences of alarm triggers integrated with laboratory or clinical test results and classified with a time series classification.

2. Background Discussion

Monitoring the health status of a patient in real time has always been of interest for healthcare providers. Over the past few decades, life-saving patient monitoring systems have become ubiquitous in modern hospitals. The alarms produced by these monitoring systems are intended to alert a caregiver to true changes in monitored physiological variables that reflect changes in the state of a patient, and thereby facilitate early intervention to correct abnormalities and to prevent unexpected patient deterioration. With modern technology, real-time access to the medical history of a patient is possible, as well as a continuous stream of physiological measurements that are often paired with alarms generated by the devices capturing these signals. All of these developments brought unintended consequences, namely, an excess of data. Clinicians are often overwhelmed by continuously streaming information. Moreover, it has been shown that the alarms produced by these devices have a high false positive rate. For cardiac monitor alarms, up to 95% of the alarms in an ICU setting are false, for example. False alarm rates of 88.8% have also been reported in other settings, which have led to alarm fatigue; a growing problem that decreases the quality of care of the patient.

It has been well recognized that threshold-based monitor alarm algorithms are intentionally set to have high sensitivity but low specificity since clinically significant conditions should never be missed. In traditional monitor algorithms, an alarm is triggered immediately when the value of the monitored parameter exceeds or falls below the preset threshold. Due to the lack of a standard for the default threshold settings, threshold-based algorithms are intentionally set to have high sensitivity in order to capture the greatest percentage of clinically significant events. As a consequence, a great number of false and nuisance monitor alarms with no clinical relevance are generated. These alarms are mainly attributable to patient movement or motion artifacts. Caregivers exposed to a large number of false and nuisance alarms become desensitized leading to alarm fatigue problems.

Alarm fatigue is developed as a result of sensory overload and desensitization due to the excessive number of monitor alarms, leading to delayed or failed responses to true clinically significant alarms and resulting in the "crying wolf" phenomenon. Excessive false and nuisance alarms may compromise the quality of patient care and cause unexpected alarm-related deaths in hospitals.

Recently, considerable efforts have been made to address the alarm fatigue issue. Combined usage of machine learning and signal processing has been proposed to reduce false alarms. Nevertheless, those approaches involved costly alarm annotation work and complex signal processing.

Accordingly, there is a need for devices and methods for reliably monitoring patient status and for accurate predictions of patient deterioration and early intervention. The present invention satisfies these needs as well as others and is generally an improvement over the art.

BRIEF SUMMARY

Patient monitors in hospitals generate a high number of false alarms that compromise patients care and burden clinicians. False alarms also obscure changing or deteriorating conditions and can delay an appropriate response by medical practitioners to patient needs. The present technology alleviates this problem by finding combinations of temporally occurring monitor alarms, laboratory test results and other medical data that are predictive of significant medical events, called SuperAlarm patterns. Matching SuperAlarm patterns to current patient conditions can trigger an alarm and are called SuperAlarm triggers. Patterns or sequences of SuperAlarm triggers can also be identified and included in the predictions of patient deterioration or of an imminent life-threatening event. Sequential SuperAlarm triggers are sequences of specific compositions of SuperAlarms that are triggered over the monitoring time of a patient data stream. Sequential patterns of SuperAlarm triggers may follow the temporal order of diseases and indicate the state of a transitioning process. Differentiating the sequential patterns of SuperAlarm triggers between clinical patients and their controls may further reduce the occurrence of false SuperAlarm triggers.

The methods preferably create a database of clinical data and laboratory test data, e.g. abnormal lab test result and delta lab test results, of patients that have the target clinical end points and a control population to discover predictive combinations of individual events. The identified predictive combinations are termed SuperAlarm patterns. Each pattern represents the co-occurrence of one or more events in a time window.

These SuperAlarm patterns are then deployed to monitor data streams in real-time. A SuperAlarm trigger can be generated when a new data sample arrives that matches with any of the pre-defined SuperAlarm patterns. In addition, each trigger may also correspond to a different SuperAlarm pattern.

Applying SuperAlarm patterns to continuously monitor a patient's data stream will result in a sequence of SuperAlarm triggers. Evaluation of the specific SuperAlarm patterns and sequence of SuperAlarm triggers can allow a caregiver to recognize and foresee unexpected patient deterioration that can lead to clinically significant events such as code blue events. Compared to conventional patient monitors, this technology has far fewer false alarms. The technology provides the additional ability of extracting predictive information from the temporal sequence of SuperAlarm triggers.

In one embodiment, there are two approaches to integrating monitor alarms with laboratory test results and then use maximal frequent itemsets mining algorithm to find SuperAlarm patterns from the integrated dataset. A final set of SuperAlarm patterns are generated by using the optimal parameters determined based on a 10-fold cross validation of the training data. Those SuperAlarm patterns are further filtered out if their false positive rates based on training data are greater than a user-specified $FPR_{max}$.

In another embodiment, an algorithm is provided that is a time series that encodes the cumulative effects of each SuperAlarm, dependent on time elapsed between the current time and the previous time each SuperAlarm patterns were triggered. This representation encodes both frequency and proximity in time, and could be easily used in any application concerned with time series classification. The time series representation accounts for both cumulative effects and temporality and is applied to code blue prediction in the intensive care unit (ICU). The health status of patients is represented both by a term frequency approach, TF and by the cumulative approach, called a "weighted accumulated occurrence representation", or WAOR. These two representations are fed into a L1 regularized logistic regression classifier, and are used to predict code blue and other clinically significant events.

The technology can also be developed into a software module that can extend the functionality of patient monitors and/or EMR systems etc. as an additional analytic module.

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawing which is for illustrative purposes only:

FIG. 1 is a schematic flow diagram of a method of identifying and applying patterns of clinical data and laboratory test data, called SuperAlarm patterns, to a real time data stream of a patient to predict potential future clinical events according to one embodiment of the technology.

FIG. 2 is a schematic flow diagram of one embodiment of a method of identifying SuperAlarm patterns from a database of medical and laboratory data.

DETAILED DESCRIPTION

Referring more specifically to the drawings, for illustrative purposes, embodiments of the apparatus and methods for detecting and applying patterns of clinical data and laboratory test data to a real time data stream of a patient to predict potential future clinical events are generally shown. One embodiment of the technology is described generally in FIG. 1 and FIG. 2 to illustrate the methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Turning now to FIG. 1, one method 10 for predicting patient deterioration by detecting patterns in heterogeneous temporal clinical data streams that are predictive of certain clinical end points and matching the patient state with those patterns is schematically shown. The detected patterns, referred to as SuperAlarm triggers, are a predictive combination of frequently co-occurring monitor alarms, conditions and laboratory test results that can predict patient deterioration or for imminent life-threatening events. SuperAlarm triggers may also exhibit patterns in the sequence of Super-Alarm patterns that are triggered over the monitoring time of a patient. Sequential patterns of SuperAlarm triggers may also indicate a temporal process of change in patient status.

At block 20 of the method of FIG. 1, at least one database of clinical data and laboratory data is assembled. A broad range of medical clinical data and laboratory data can be assembled for evaluation. For example, the data can include an abnormal laboratory test result or simple patterns of two consecutive laboratory results such as normal to normal, normal to high, normal to extremely high etc. or it can be a change in a laboratory test result over a threshold. The data can also be various alarms from medical devices, such as a patient monitor or an alert from a medical device like a ventilator. It can be physiological conditions from analyzing physiological signals, e.g., ECG PR interval greater than 140 mill-seconds or it can be more complex trending patterns, e.g., when the duration of ECG PR interval prolongation is more than 3 hours.

The data can also be temporal such as the start of a medication or the completion time of an operation or a procedure. Known clinical events, sequences and associations as well as any nursing or physician charted events in clinical notes can be included in the database at block 20.

The next step of the method at block 30 is to mine at least one database of clinical data from a cohort of patients that have the target clinical end points and a control cohort to discover predictive combinations of individual events. The identified predictive combinations at block 30 are termed SuperAlarm patterns. SuperAlarm patterns are predictive combinations of frequently co-occurring monitor alarms, conditions and laboratory test results (abnormal lab test and delta lab test results), for example. Each pattern represents the co-occurrence of one or more events in a time window. The number of discovered SuperAlarm patterns from a given database will depend on the algorithm parameters that essentially control the tradeoffs between sensitivity and specificity.

The preferred methods for discovering SuperAlarm patterns at block 30 from the database assembled at block 20 are described in detail in Example 1 through Example 3 below. These methods not only identify SuperAlarm patterns of co-occurring conditions and laboratory results, they also provide the additional ability of extracting predictive information from the temporal sequence of SuperAlarm patterns.

Once SuperAlarm patterns are identified at block 30, the SuperAlarm patterns are then deployed to monitor data streams of current patients in real-time at block 40 of FIG. 1. The stream of data of a particular patient can be compared to the library of SuperAlarm patterns over time. A SuperAlarm trigger at block 50 can be generated when a new data sample arrives that matches any of the pre-defined SuperAlarm patterns. By applying SuperAlarm patterns continuously to monitor the data stream of a patient will result in a sequence of SuperAlarm triggers at block 50.

In addition, each trigger may correspond to a different SuperAlarm pattern so that the different triggers can be evaluated over time to identify patterns of SuperAlarm triggers. Accordingly, sequences and patterns of SuperAlarm triggers that are triggered over the monitoring time by a patient can also be evaluated as part of the process. Sequential patterns of SuperAlarm triggers may indicate a temporal process of change in the status of a patient. Differentiating the sequential patterns of SuperAlarm triggers between patients and their controls may further reduce false SuperAlarm triggers (increasing specificity) as well as identify temporal patterns in these SuperAlarm triggers. A SuperAlarm alert at block 50 can be generated when a new data sample from a patent arrives that not only matches any of the pre-defined SuperAlarm patterns but also when there are characteristic sequences of SuperAlarm triggers observed.

To further recognize the temporal patterns in these SuperAlarm triggers at block 50 of FIG. 1, a variety of off-the-shelf classifiers can be applied to classify a sequence of SuperAlarm triggers into those that predict the target clinical end point and those that are from control cohort.

However, a necessary step before applying an off-the-shelf classifier to a sequence of SuperAlarm triggers is to represent this sequence as a vector of a fixed dimension so that these classifiers can handle the sequence. There are several ways that this can be done.

One way of representing a sequence is to simply calculate the occurrence frequency of each SuperAlarm pattern using the following equations:

$$f_i(T) = \frac{1}{\Delta t} \sum_{t=T-\Delta t}^{T} h_i(t)$$

where $h_i(t) =$ $$\begin{cases} 1 & \text{if the } i\text{-th SuperAlarm pattern is triggered at time } t \\ 0 & \text{if the } i\text{-th SuperAlarm pattern is not triggered at time } t \end{cases}$$

then the vector $F(T)=[f_1(T), f_1(T), \ldots, f_N(T)]$ is a vector representation of a SuperAlarm sequence between time $T-\Delta t$ and $T$ where N is the total number of distinctive SuperAlarm patterns deployed.

Another way of representing a sequence is to weight each trigger differently. As illustrated in Example 1, the frequency of the SuperAlarm sequences is used having a given SuperAlarm pattern as weights.

$$f_i(T) = \log\left(1 + \frac{1}{\Delta t} \sum_{t=T-\Delta t}^{T} h_i(t)\right) \times \log\left(\frac{M}{1 + \left[\begin{array}{c}\text{number of sequences having at least}\\\text{one } i\text{-th SuperAlarm pattern triggered}\end{array}\right]}\right)$$

where M is the total number of SuperAlarm sequences in the training data set.

Yet another way of representing a sequence is to weight each trigger by introducing an age factor as illustrated in Example 2, an approach termed weighted accumulated occurrence representation.

$$f_i(T) = \sum_{t=0}^{T} w(T-t) \times h_i(t)$$

where $T-t$ is the age of the trigger at time t, the closer t is to the current time T, the smaller the age. Typically, smaller age should carry more weight. Therefore, several forms of the function $w(T-t)$ can be designed.

For example, $$(T-t) = \frac{1}{\sqrt{T-t}+1}, w(T-t) = \frac{1}{T-t+1} \text{ or } w(T-t) = \frac{1}{(T-t)^2+1}$$

are suitable. Or a more general function that has three parameters controlling the amount of weight at different ages can be used such as $$w(T-t) = \frac{1}{[(T-t)/\beta]^\alpha + \gamma}.$$

In another embodiment, performance metrics are used to measure accuracy. There are three performance metrics for measuring how SuperAlarm performs in predicting a chosen clinical end point that are preferred. These metrics include:

1. Alarm frequency reduction rate (AFRR) where:

$$(AFRR) = 1 - \frac{[\text{hourly number of SuperAlarm triggers}]}{[\text{hourly numbers of raw events}]}.$$

2. Sensitivity@T=percentage of patients with the chosen clinical end point who have at least one positive SuperAlarm trigger and/or positive sequence classifier output in a 12-hour window (or n-hour window) that precedes the time of the chosen clinical end point by at least T hours.

3. Work-up to detection ratio (WD) if a sequence representation is used to classify a sequence of SuperAlarm triggers where:

$$(WD) = \frac{[\text{number of patients with SuperAlarm triggers}]}{\begin{bmatrix} \text{number of coded patients with} \\ \text{SuperAlarm triggers} \end{bmatrix}} \text{ or}$$

$$(WD) = \frac{[\text{number of patients with positive classifier outputs}]}{\begin{bmatrix} \text{number of coded patients with} \\ \text{positive classifier outputs} \end{bmatrix}}.$$

Weighting of a SuperAlarm pattern trigger can be achieved by combining the age factor and the frequency of the SuperAlarm sequences having a given SuperAlarm pattern. Weighting of a SuperAlarm pattern trigger can be also achieved by factoring certain performance metrics of individual SuperAlarm patterns, e.g., information gain.

Finally, at block 60 of FIG. 1, the SuperAlarm patterns and SuperAlarm trigger patterns are evaluated to predict the advent of potential future clinical events in the current patient. A clinical response to the alarm can also be formulated. A wide variety of clinical end points can be predicted using SuperAlarm patterns and trigger patterns including: cardiopulmonary arrest—code blue; unplanned ICU transfer; mortality; acute lung injury; acute intracranial pressure elevation and acute hypotension etc.

The technology described herein may be better understood with reference to the accompanying examples, which are intended for purposes of illustration only and should not be construed as in any sense limiting the scope of the technology described herein as defined in the claims appended hereto.

EXAMPLE 1

In order to demonstrate the technology, two approaches to integrate monitor alarms with laboratory test results and then use maximal frequent itemsets mining algorithm to find SuperAlarm patterns from the integrated dataset were tested. A final set of SuperAlarm patterns were generated by using the optimal parameters determined based on a 10-fold cross validation of the training data. Those SuperAlarm patterns were further filtered out if their false positive rates based on training data were greater than a user-specified $FPR_{max}$.

The performance of SuperAlarm patterns were assessed in two aspects using an independent test data set not used in the training phase. In the first aspect, sensitivity with respect to prediction window and sensitivity with respect to lead time, respectively were calculated. In the second aspect, the ratio of a number of SuperAlarm triggers to that of the monitor alarms for control patients were calculated. Performance of SuperAlarm patterns composed of both monitor alarms and laboratory test results were compared to that of SuperAlarm patterns composed of only monitor alarms under four $FPR_{max}$ values (0.02, 0.05, 0.10, and 0.15). Statistically significant improvement by adding laboratory test results to SuperAlarm clinical data was demonstrated under all $FPR_{max}$ values. Depending on the values of $FPR_{max}$, SuperAlarm patterns composed of monitor alarms and last two results ranging from 21 to 36 laboratory tests were triggered at least once among 56.7% to 93.3% of code blue patients in a one-hour window preceding the events while their frequency was only 2.0% to 14.8% of that of regular monitor alarms for control patients.

Referring now to FIG. 2, a method 100 for determining SuperAlarm patterns is schematically shown. At block 110, the raw data is pre-processed to unify the names of monitor alarms and to exclude crisis alarms. Initially, names of monitor alarms related to the same physiological variable are unified by ignoring differences in terms of monitor ports to which the sensors were attached. In addition, at block 110 "crisis" monitor alarms signaling asystole, ventricular fibrillation, and no breath are excluded. Our ultimate goal is to predict code blue and other clinically significant events. Therefore, exclusion of these "crisis" alarms, which usually occur near code blue events, may avoid artificially increasing the prediction sensitivity of the SuperAlarm set.

Monitor alarms preceding the code blue events were extracted. There were 37 case patients in the data set having more than one code blue call and only alarms prior to the first code blue call extracted for analysis. 662,576 raw monitor alarms for code blue patients and 5,363,019 for control patients were collected. The monitoring time was 250.3±406.1 hours and 279.9±384.3 hours for the case patients and control patients, respectively. Hourly number of monitor alarms was 18.9±27.9 per code blue patient and 9.5±9.8 per control patient. Within a 5 minutes window preceding code blue event, the number of code blue patients having at least one "crisis" monitor alarms signaling asystole, ventricular fibrillation and no breath was 38(15.0%), 31(12.2%) and 3(1.2%), respectively.

Laboratory test results from 19 laboratory test panels were extracted, resulting in a total 65 types of laboratory tests. There were 191,483 and 362,960 laboratory results for code blue and control patients, respectively. For code blue patients, 37.1% of laboratory test results were flagged as H while 34.7% as L, 24.9% as N, 2.5% as LL and 0.8% as HH. For control patients, 45.5% of laboratory test results were flagged as H while 41.2% as L, 10.7% as N, 1.8% as LL and 0.8% as HH. It should be noted that the majority of laboratory test results for both case patients and control patients were flagged as either H or L, indicating abnormalities were common in the laboratory test results among these patients.

At block 120, patients with abnormally small number of monitor alarms were excluded. It was found that some code blue patients had extremely small number of alarms within a $T_w$-long time window preceding code blue events. Given the retrospective nature of this study, it was impossible to determine the exact reasons why this occurred. Including these patients to extract SuperAlarm patterns will provide incorrect results when determining the incidence of an alarm or alarm combinations among the code blue patients. Therefore, these patients were excluded from the study based on an objective criterion.

The minimum number of alarms (called minimum-alarm-count-threshold) within a $T_w$-long time window immediately preceding code blue events was estimated. As monitor alarms becomes more frequent near onset of code blue events, it was assumed that the arrival of monitor alarms follows Non-Homogenous Poisson Process (NHPP) with non-linear rate.

We denoted $\mu_t$ as occurring-rate of alarms at t over time interval (0,T] such that $\mu_t = e^{\alpha + \beta t}, 0 \le t \le T$.

The time interval (0,T] is divided into N subintervals $$\left( \frac{(k-1)T}{N}, \frac{kT}{N} \right],$$

$1 \le k \le N$. The term $y_k$ represents the average number of alarms per patient over the subinterval k, we then utilize generalized linear model (GLM) to estimate parameters $\alpha$ and $\beta$.

The estimated number of alarms over $T_w$ is given by $\hat{n} = \int_0^{T_w} \mu_t dt = \int_0^{T_w} e^{\alpha + \beta t} dt$ 95% interval of $\hat{n}$ is $(n_{lower}, n_{upper})$.

Thus, the minimum-alarm-count-threshold over the $T_w$ is defined as $N_{minCount}=\lfloor n_{lower} \rfloor$ where $\lfloor x \rfloor$ is the maximum integral number that is not greater than x.

After calculating $N_{minCount}$, the code blue patients whose number of alarms is below this threshold within a $T_w$-long time window preceding code blue events can be excluded. Monitor alarms from the rest of patients constitute the Alarm data set.

Then, the monitor alarms were integrated with laboratory test results at block 130 of FIG. 2. Two approaches were developed to integrate monitor alarms with laboratory test results. In the first approach, the latest abnormal result of each type of laboratory tests were integrated with the array of monitor alarms within a $T_w$-long window. Abnormal laboratory test results from the dataset were picked based on the associated flags as reported by the electronic medical record (EMR) system. There were five flags for the reported laboratory test results against the reference range: HH (extremely high), H (high), L (low), LL (extremely low) and N (normal). The abnormality flags for a given laboratory test result will therefore include HH, H, L and LL.

In the second approach, the difference between the last two results of a laboratory test before a $T_w$-long window were used as a laboratory test trigger to be integrated with monitor alarms. Each laboratory test result can have five flags HH, H, L, LL, N and hence 25 possible delta laboratory test results: [HH→HH, HH→H, HH→L, HH→LL, HH→N, ..., N→HH, N→H, N→L, N→LL, N→L]. For instance, if the last two results of laboratory test "Hemoglobin" were flagged by N and L, then the delta laboratory test result would be represented as "Hemoglobin N→L".

Based on these two approaches, two extended datasets were created, namely, the Ab Lab+Alarm dataset, which is composed by the Alarm dataset integrated with abnormal laboratory test results, and the Delta Lab+Alarm dataset, which consists of the Alarm dataset integrated with delta laboratory test results.

SuperAlarm patterns were then discovered at block 140 and a final SuperAlarm set under optimal algorithmic parameters is generated. To facilitate discovering SuperAlarm patterns, the parametric monitor alarms are encoded by discretizing their numeric values using the Class-Attribute Contingency Coefficient(CACC) algorithm. Laboratory test results do not need to be encoded since they are not represented with numeric values. The integrated laboratory test results and encoded monitor alarms within $T_w$-long window immediately preceding code blue events are then used to mine maximal frequent itemsets (MFI), i.e., SuperAlarm candidates.

Definition 1—Support of an itemset: The support of an itemset is defined as the proportion of code blue patients in the data set who contain the itemset.

Definition 2—Frequent Itemsets (FI): An itemset is frequent if its support is not less than a user-specified threshold minimum support (i.e., min_sup).

Definition 3—Maximal Frequent Itemsets (MFI): An itemset is maximally frequent if none of its superset is a frequent itemset. A superset of an itemset is an extension of the itemset.

It should be noted that the following relationships hold between MFI and FI: MFI⊆FI. Classic Apriori-based methods to mine FI employ a breadth-first traversal of the search space to find support information for all k-itemset (k=1, 2, 3, ... ). This method scans all 2k−2 subsets of each k-itemset to determine whether the itemset is frequent or not based on the Apriori-principle, stating that the superset of any non-FI set is still a non-FI set. Apriori-based method is computationally expensive when the dataset is huge or the frequent itemsets are very long. A different method called maximal frequent itemset algorithm (MAFIA) was used to mine MFI and it overcame this shortage.

MAFIA mines MFI using depth-first traversal on a lexicographic itemset lattice. Each node on the lattice includes head and tail. The head contains an itemset identifying the node while the tail contains frequent extensions of items lexicographically greater than any items of the head. In the process of depth-first traversal, each item in the node's tail is determined and counted as a 1-extension. According to the Apriori-principle, the traversal process will stop if the support of {node's head}∪{1-extension} is less than a user-specified min_sup. A candidate itemset will be added into MFI set if no superset of this candidate itemset exists in the MFI set. Three pruning strategies were applied to reduce the search space. These include: 1) parent equivalence pruning (PEP); 2) frequent head union tail pruning (FHUT); and 3) head union tail MFI (HUTMFI). MAFIA employs vertical bitmap to represent data and uses an adaptive compression technique to enhance the performance.

In order to utilize MAFIA to mine MFI, a vertical bitmap B was built to represent laboratory test results and encoded monitor alarms extracted within $T_w$-long window immediately preceding code blue events. Vertical bitmap $B=\{x_{ij}\}$ is a M×N matrix, where M is the number of code blue patients and N is the number of encoded monitor alarms and laboratory test results ($1 \leq i \leq M$, $1 \leq j \leq N$). $x_{ij}=0$ if the $i^{th}$ patient does not have the $j^{th}$ alarm or laboratory test result, otherwise $x_{ij}=1$. Vertical bitmap B was then input into MAFIA under the user-specified value of min_sup. As the process of searching goes down the lattice, the head of the node on the lattice grows longer. Due to the sparseness of bitmap especially at the lower support levels, MAFIA compresses the bitmap by removing the bit for patient P from itemset X if P does not contain X because MAFIA only needs information about the patients who contain the itemset X to count the support of the subtree rooted at node n. MAFIA employs an adaptive compression scheme to determine when to compress the bitmap. In the meanwhile, the three pruning strategies are applied to remove non-maximal sets and therefore reduce the search space. MAFIA adopts the progressive focusing technique to check whether the extracted maximal frequent itemsets are complete or not. MAFIA outputs MFI which is a set of maximal patterns consisting of potential components of laboratory test results and monitor alarms.

Finally, at block 160 of FIG. 2, the final SuperAlarm patterns are evaluated by performing offline and simulated online analysis. Monitor alarms and laboratory test results from a randomly selected 20% of both code blue patients and control patients compose the independent test data set for the simulated online analysis. Those from the remaining 80% of both groups of patients constitute the training data set that is used to set up a conventional 10-fold cross validation set (10-fold CV set) in the offline analysis phase. Optimal parameters of the algorithm are determined based on the performance of the SuperAlarm candidates generated by MAFIA from the 10-fold CV set. The final SuperAlarm set is then generated from the whole training data set under the optimal parameters. This final SuperAlarm set is eventually employed to perform simulated online analysis.

To find the final SuperAlarm patterns using Offline analysis to determine optimal algorithm parameters and generate the final SuperAlarm set, we need the optimal values of algorithm parameters of $T_w$-long time window and minimum support min_sup were determined first. This was done by performing cross-validation analysis. Monitor alarms and laboratory test results within $T_w$-long window were extracted immediately preceding code blue events from the first nine folds of the 10-fold CV set. MAFIA is employed to generate SuperAlarm candidates from the extracted data set under a user-specified value of min_sup. The SuperAlarm candidates are then applied to the first nine folds of the 10-fold CV set from control patients to obtain false positive rate (FPR) values for each of the SuperAlarm candidates. FPR of a SuperAlarm pattern was defined as the percentage of $T_w$-long windows that trigger this pattern from control patients. This was achieved by partitioning the training data set of control patients into consecutive 4-hour windows from the beginning of monitoring to the end. A $T_w$-long window was randomly picked within each of these 4-hour windows. Laboratory test results and monitor alarms within the $T_w$-long window are used to determine whether the SuperAlarm pattern is triggered, and thereby the FPR of the SuperAlarm pattern is obtained. A SuperAlarm candidate will be removed if it has FPR value greater than a given threshold.

After removing disqualified SuperAlarm candidates, the final SuperAlarm patterns were applied to the remaining fold of the 10-fold CV set to obtain a pair values of true positive rate (TPR) and false positive rate (FPR). TPR was defined as the percentage of code blue patients who trigger at least one of SuperAlarm candidates within a $T_w$-long window. FPR here was calculated in terms of percentage of $T_w$-long windows that trigger any of the SuperAlarm candidates from control patients. Varying the threshold will lead to various pairs of TPR and FPR, and hence a receiver operation characteristic (ROC) curve can be generated. This process was repeated for each of the 10 folds, resulting in 10 ROC curves. The final ROC curve is obtained by averaging the 10 ROC curves under a given algorithm parameter combination of $T_w$-long window and _sup.

Given a user-specified maximal false positive rate ($FPR_{max}$), the optimal values for $T_w$ and min_sup were determined by choosing the one with maximal TPR value across all algorithm parameter combinations while possessing FPR value less than $FPR_{max}$. Under the optimal algorithm parameter combination, MAFIA is applied again to the whole training data to discover the complete SuperAlarm candidates. The whole training data is created by coalescing the 10-fold CV data set into one single set. These complete SuperAlarm candidates are further refined to generate final SuperAlarm patterns by filtering out those patterns whose FPR values are greater than $FPR_{max}$.

Simulated online analysis at block 160 of FIG. 2 was conducted after discovering the final SuperAlarm patterns. The independent test data set was used to simulate the application of these SuperAlarm patterns in real-time and to assess the performance of predicting code blue events.

At the moment of receiving a new monitor alarm or a new laboratory test result, the algorithm will determine if any of the final SuperAlarm patterns can be found among the integrated laboratory test results and monitor alarms within a $T_w$-long window preceding the time of this new measurement. It should be noted that $T_w$ is the optimal length of the time window determined in the training process.

By running the simulation across the sequence of monitors alarms and laboratory test results for a given patient, a new sequence of SuperAlarm triggers is obtained. Three metrics were used to assess the performance of the SuperAlarm set predicting code blue events:

(1) Sensitivity function with respect to prediction window. This metric is calculated in terms of percentage of code blue patients triggering any of the final SuperAlarm patterns within prediction window immediately preceding code blue events. This is the same definition used in our previous work.

(2) Sensitivity function with respect to lead time. This metric is computed in terms of percentage of code blue patients triggering any of the final SuperAlarm patterns within a time window that starts at 12-th hour and ends at a lead time preceding code blue event.

(3) False SuperAlarm ratio. This metric is obtained as the ratio of hourly number of the final SuperAlarm triggers for control patients to that of regular monitor alarms, or that of regular monitor alarms plus laboratory test results if the final SuperAlarm patterns contain laboratory test results.

For a given $FPR_{max}$, the McNemar's test was also performed to determine whether the performance of one of the three SuperAlarm sets generated from Alarm data set, Ab Lab+Alarm data set and Delta Lab+Alarm data set is significantly different from each other using the independent test data set. To do this, the data of each control patient was first partitioned into consecutive 4-hour windows from the beginning of monitoring to the end. The McNemar's test was then performed by done by randomly selecting one of the 4-hour windows for each control patient. In this way, the dependence of these consecutive 4-hour windows can be avoided. Any two types of the three SuperAlarm sets were applied to both the data of control patients within the selected 4-hour window and the data of code blue patients within the optimal $T_w$-long window preceding code blue events, respectively. This process of the McNemar's test was repeated N times. The performances of two types of SuperAlarm sets were considered to be significantly different if the number of significant McNemar tests (p<0.05) is greater than 95% of total repeated tests.

The results showed that the sensitivity of predicting code blue events one hour in advance obtained by the SuperAlarm set generated from Ab lab+Alarm data set and from Delta lab+Alarm data set outperform that obtained by the SuperAlarm set consisting of only monitor alarms. Accordingly, by integrating patient data and assessing clinical patterns of multiple alarms and associated vital signs holistically instead of a single alarm in isolation may deliver meaningful messages to a clinician and improve patient safety.

EXAMPLE 2

To further demonstrate the operational principles of the methods, a time series that represents the cumulative effects of each SuperAlarm, dependent on time elapsed between the current time and the previous time each SuperAlarm patterns were triggered, was generated. This representation encodes both frequency and proximity in time, and could be easily used in any application concerned with time series classification. SuperAlarm patterns are combinations of frequently co-occurring monitor alarms and laboratory test results that were capable of predicting code blue events in hospitalized patients. The SuperAlarm patterns were then discovered using a maximal frequent itemsets mining algorithm. They were further filtered by excluding patterns that were present only in a very small number of patients that had a high false positive rate.

The dataset used to extract the SuperAlarm patterns was extracted from a central repository of comprehensive data elements archived for patients hospitalized at the UCLA Ronald Regan Medical Center, admitted from March 2010 to June 2012. The patients included in this study came from either ICUs or other acute care areas. The control set was determined as patients without code blues or unplanned ICU transfers. For each code blue patient, a cohort of control patients was selected following certain criteria: The same APR DRG (All Patient Refined Diagnosis Related Group) or Medicare DRG; the same age (±5 years), the same sex, and they had to be admitted to the same hospital unit within the same month. A total of 1766 control patients and 176 code blue patients were included in the training set, and 440 control and 30 code blue patients in the test set.

A continuous, cumulative representation of the lingering effect a Super Alarm trigger should have is used. In this representation, the i-th entry will describe the cumulative value, up to time t, of the i-th SuperAlarm.

More specifically, $$p_{cont}(t, w) = \begin{pmatrix} y_1(t) \\ \vdots \\ y_m(t) \end{pmatrix} = \begin{pmatrix} \sum_{t' \leq t} w_1(|t-t'|)x_1(t') \\ \vdots \\ \sum_{t' \leq t} w_m(|t-t'|)x_m(t') \end{pmatrix}$$

where the indicator function $\chi_i(t')$ is defined as:

$$x_i(t') = \begin{cases} 1, & \text{if } i\text{-}th \text{ SuperAlarm is triggered at time } t' \\ 0, & \text{else} \end{cases}.$$

and $w_i(|t-t'|)$ is a decreasing function of $|t-t'|$, the difference between the current time t and the time the i-th SuperAlarm was triggered, t' and 0 otherwise.

This is because, if a SuperAlarm is triggered, we want it to influence the i-th entry of p(t) for minutes, or hours. Possible choices for this function include:

$$w_i(|t-t'|) = \frac{1}{\sqrt{|t-t'|+1}} \quad \text{a)}$$

$$w_i(|t-t'|) = \frac{1}{|t-t'|+1} \quad \text{b)}$$

$$w_i(|t-t'|) = \frac{1}{|t-t'|^2+1} \quad \text{c)}$$

All patients yield a sequence of vectors $p(t_1), p(t_2), \ldots$ where $t_i$ is a time point where any SuperAlarm was triggered. We chose time points $t_1, \ldots, t_N$ for each patient. For control patients, no particular time carries more importance. Hence, time points $t_i$ for this population will be sampled uniformly from all the time points t when a SuperAlarm was triggered. Up to three time points for each control patient were sampled. However, out of the 1766 control patients, 393 had zero SuperAlarm triggers, 420 had up to one, and 451 had up to 2 SuperAlarm triggers. We did not sample any of the patients with zero SuperAlarm triggers. Since we had far more controls than cases, we oversampled the cases, as to have a more rich set from which to learn the underlying patterns. In a code blue patient, time points closer to a code blue event should be preferred, since they give us vectors p(t) that carry a more predictive power for a code blue event. However, patients have a variable length of recording time. For records with more than 6 hours of duration, we sampled time points $t_i$ uniformly at random as follows: 30 time points from the code blue event up to two hours before the event, 20 points from 4 hours before the event to 2 hours before the event, and 10 points from 6 hours up to 4 hours before the event. If the length of the record was less than 6 hours, we sampled 60 time points uniformly at random from the whole record. Hence, the training set consists of 7566 observations. The data is scaled to the range [0,1], and the transform was then applied to the test set.

The test set of patients were sampled in two different ways. First, it was sampled in the same manner as the training set was sampled: up to three samples per control patient and 60 per code blue patient, with the time points selected as in the previous section. However, we also want to simulate an online analysis, in which every time a SuperAlarm is triggered, the algorithm has to decide whether this patient is at risk of a code blue event. In this second analysis, both control and code blue patients in the test set were sampled every time a SuperAlarm is triggered, producing the sequence $(t) = \{p(t_1), p(t_2), \ldots, p(t_N) | t_i \in T_{SA}\}$, where $SA = \{t_i \text{ such that a SuperAlarm was triggered at time } t_i\}$. For the first approach, 1024 control samples and 1165 code blue ones were obtained. For the second approach, 70,000 code blue and 200,000 control vectors were produced.

The extracted data comes from either the frequency formulation $p_{freq}$, which produces sparse vectors; or from the continuous formulation $P_{cont}$, which creates a more dense representation. Initially, the number of features in the vectors was reduced. Originally, we had 428 dimensional observations. We applied a L1 regularized logistic regression model to the training data. Linear models penalized with the L1 norm have sparse solutions: many of their estimated coefficients are zero. When the goal is to reduce the dimensionality of the data to use with another classifier, they expose a transform method to select the non-zero coefficients. In all sets we used the parameter C=0.5, the parameter C controls the sparsity: the smaller C, the fewer features selected.

For classification, an L1 Logistic Regression (L1-LR) classifier was used, where the probability of a sample x being labeled as a code blue (y=1) is given by:

$$p(y=1|x;\theta) = \sigma(\theta^T x) = \frac{1}{1+\exp(-\theta^T x)},$$

where x is a vector whose i-th entry carries information about the i-th SuperAlarm pattern, either frequencies or cumulative effects, and $\theta$ is a vector of weights to be learned by the classification algorithm, given by the solution to:

$$\min_\theta \Sigma_{i=1}^M -\log p(y^{(i)}|x^{(i)}; \theta) \text{ subject to } \|\theta\|_1 \leq C.$$

L1-LR is a fast algorithm. Its L1 regularization term ensures many of the coefficients in the representation will go towards zero, which makes it amenable for high-dimensional problems. Moreover, it suits well both sparse and dense data. It also has only one hyper parameter to adjust, namely, the parameter encoding the strength of the regularizer C. We trained the L1-LR classifier. The hyper parameter C, as well as the class weights, were chosen via a grid search and 10-fold cross validation on the training set. The lower bound $C_{min}$ for the L1 penalization term C was calculated in order to get a non-null (all feature weights to zero) model. Afterwards, 30 values spaced logarithmically from 0 to 4 were chosen and considered the grid to be those values multiplied by $C_{min}$. The value of C that is chosen maximizes the mean of a given performance metric across all the folds in cross validation in the training set. However, different performance metrics produce different results in the hyperparameters of the classifiers. There are several performance metrics to gauge how well an algorithm performs, and there are always trade-offs. For example, maximizing sensitivity, that is, proportion of true positives identified by our classifier, often comes at the expense of an increase in the false positives. The analysis was performed with the following four performance metrics:

1) Precision: The proportion of true code blue patients out of all the patients labeled as "code blue" by our algorithm. Often, less detections are made but a higher proportion of these detections are correct. It's given by TP/(TP+FP) where TP=true positive, FP=False positive.

2) F1: This is the harmonic mean between sensitivity and precision and it balances the trade-off between precision and sensitivity. It is given by f1=2 TP/(2TP+FP+FN), where FN=False negative.

3) ROC AUC: Area under the ROC curve can be interpreted as the probability that the algorithm will assign a higher score to a randomly chosen code blue patient example than to a randomly chosen control patient.

4) Partial AUC: This is the area under the ROC curve for false positive rate (FPR) less than a given threshold and in the case FPR=0.15.

Results for each one of these metrics are presented as the performance metrics to be optimized during cross validation. An online time series classification was also made. Both control and code blue patients in the test set were sampled every time a SuperAlarm was triggered, producing a sequence $p(t) = \{p(t_1), p(t_2), \ldots, p(t_N) | t_i \in T_{SA}\}$. Using the classifier trained on the training set, this sequence can be replaced by a sequence of decisions of the classifier, namely, $\{y_1, y_2, \ldots, y_N\}$, where y=0 or y=1, with y=0 corresponding to the classifier labeling the observation as "control", and y=1 to the classifier labeling the observation as "code blue".

Several performance metrics were utilized to evaluate the precision of the classifications and predictions to further validate the methods.

1) SensitivityL@(T): The sensitivity of the algorithm for each of the time series representations p(t), both the frequency based and continuous representations was computed. However, we want to determine with how much anticipation before the code blue our algorithm predicts it. "SensitivityL@(T)" is defined to be the proportion of code blue patients to have at least one y=1 in the time window [T hours before the code blue–12 hours, T hours before code blue event]. One expects, as T increases, that is, the farther away our time window is from the code blue, the SensitivityL@(T) decreases.

2) Work-up to detection ratio: The work-up to the detection ratio is defined as WTDR=(a+b)/a, where a is the number of code blue patients that the algorithm correctly labeled as "code blue", and b is the number of control patients that the algorithm incorrectly labeled as "code blue".

3) False SuperAlarm ratio: The False SuperAlarm ratio (FSAR) is defined as number of SuperAlarm triggers in one hour divided by number of monitor alarms in that hour. This quantity was computed for each control patient, randomly choosing a total of 100 one hour segments randomly across their total hospital stays and obtaining the mean per patient. Afterwards, we report the total mean and standard deviation (std) across all control patients.

In computing the WTDR, a window of 12 hours was specified corresponding to a usual nursing shift. The algorithm labeled a "code blue" patient as true if at least one y is equal to 1, from the time of the code blue up to 12 hours before the code blue. To determine if the algorithm labeled a control patient as a "code blue" patient, a 12 hour window throughout the patient's stay was randomly selected, and, if there was at least one y=1 in this time window, the patient was labeled as a "code blue." However, since this is a random estimation, this window selection process was repeated 100 times, and a mean m and standard deviation (std) s was reported. This procedure produced a sequence $\{(m_1, s_1), \ldots, (m_n, s_n)\}$, where n was the number of control patients in the test set. Finally, the random variable b, that represents the number of control patients classified as "code blue", is given by the following:

$$\text{mean}(b) = \sum_i m_i, \text{std}(b) = \sqrt{\sum_i s_i^2}$$

$$\text{mean}(WTDR) = \frac{a + \text{mean}(b)}{a} = 1 + \frac{\text{mean}(b)}{a},$$

$$\text{std}(WTDR) = \frac{\text{std}(b)}{a}$$

Using the f1 score as a performance metric, it was shown that the cumulative approach, with the function sq, clearly outperforms the other ones, in terms of SensitivityL@(T) and with a WTDR of 4.75 and a FSAR of 0.11. When precision is used as a performance metric, the sensitivity drops significantly for all six approaches. However, the cumulative approaches (sq, abs and sqrt) have a higher sensitivity than the frequency ones, while keeping comparable WTDR and FSAR. When using the ROC AUC as the performance metric to be optimized in cross validation, the sensitivities for all approaches except sqrt are comparable, as are their WTDR and FSAR. However, the sq approach with the f1 score still gives us the same sensitivity and a lower WTDR and FSAR. Finally, freq 2 and sq are the most sensitive approaches when suing the Partial AUC metric, but freq 2 has a WTDR and a FSAR that are significantly higher than those of sq. In conclusion, the cumulative approach with the function sq has performed better in the three clinically significant metrics: SensitivityL@(T), WTDR and FSAR.

EXAMPLE 3

To further demonstrate the methods, in-hospital code blue events were predicted using a term frequency inverse document frequency based kernel. As illustrated in Example 2, the maximal frequent combinations of monitor alarms and laboratory test results (e.g. SuperAlarm patterns), were shown to be capable of predicting code blue events in hospitalized patients.

This approach was further developed to differentiate the patterns in the sequence of SuperAlarm triggers between coded patients and their controls with the goal of further reducing false SuperAlarm triggers. This embodiment is based on using support vector machine (SVM) with term frequency inverse document frequency (TFIDF) based kernel to measure the distance between two sequences of SuperAlarm triggers.

SuperAlarm sequences were generated for both code blue patients and control patients by applying the SuperAlarm patterns to the sequence of monitor alarms and laboratory test results. To train SVM, six-hour long subsequences immediately prior to the onset of code blue events are selected as positive examples. For negative examples, six-hour long subsequences are randomly selected over the whole SuperAlarm sequence of control patients. These six-hour long subsequences are represented by TFIDF. We then calculate the TFIDF-based kernel that measures the similarity of two 6-hour long subsequences. The performance of the SVM was further evaluated using 5-fold cross-validation. Online simulation was analyzed and performances of the method are evaluated in terms of the sensitivity that is defined as the percentage of code blue patients classified correctly (i.e., true positive) by the decision function within $T_p$-long prediction window immediately preceding code blue event, and the false positive ratio (FPR) which is the percentage of number of hourly subsequence for control patients which is predicated incorrectly (i.e., false positive).

254 code blue patients (age=61.6±8.2 years) and 2,213 control patients (age=63.5±14.6 years) admitted during March 2010 to June 2012 at UCLA Medical Center were involved in the present study. 662,576 monitor alarms and 191,483 laboratory test results for code blue patients and 5,363,019 monitor alarms and 362,960 laboratory test results for control patients were extracted, respectively. 428 SuperAlarm patterns that were found were used to generate SuperAlarm sequences for code blue patients and control patients. The result of 5-fold cross validation shows that the average area under curve (AUC) is 0.8300±0.0455. The online simulation results demonstrate that the method is capable of predicting in hospital code blue event two hours in advance with a sensitivity of 94.74% and a FPR of 8.03%±0.2321.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A method of identifying and predicting patient clinical status changes, the method comprising: (a) creating a database of medical data and laboratory data of a pool of healthy and unhealthy patients; (b) identifying patterns of temporally occurring clinical events and laboratory results of unhealthy patients with target conditions; (c) comparing a clinical data stream of a patient with the identified patterns to identify matching patterns; and (d) predicting a medical status of the patient based on a sequence of observed matching patterns.

2. The method of any preceding embodiment, further comprising: triggering a monitor alarm when an identified pattern matches data points in a patient data stream.

3. The method of any preceding embodiment, further comprising: collecting sequences of matching patterns of patients in a pool of healthy and unhealthy patients; comparing collected sequences observed matching pattern sequences of a patient data stream; and evaluating matching sequences of patterns of the patient data stream.

4. The method of any preceding embodiment, further comprising: using a maximal frequent itemsets mining algorithm to find patterns from the integrated dataset; generating a final set of patterns by using optimal parameters determined by a 10-fold cross validation of training data; and filtering out patterns if their false positive rates based on the training data are greater than a user-specified $FPR_{max}$; wherein the method is performed by executing programming on at least one computer processor, the programming residing on a non-transitory medium readable by the computer processor.

5. The method of any preceding embodiment, further comprising: integrating latest abnormal results of each type of laboratory tests with an array of monitor alarm data within a $T_w$-long window; selecting abnormal laboratory test results from the dataset based on the associated flags as reported by an electronic medical record (EMR) system; using the difference between last two results of a laboratory test before a $T_w$-long window as a laboratory test trigger to be integrated with monitor alarms; creating two extended datasets comprising: a Ab Lab+Alarm dataset comprising an Alarm dataset integrated with abnormal laboratory test results; and a Delta Lab+Alarm dataset, which consists of the Alarm dataset integrated with delta laboratory test results; encoding parametric monitor alarms by discretizing their numeric values using the Class-Attribute Contingency Coefficient (CACC) algorithm; evaluating the patterns by performing offline and simulated online analysis; and performing offline analysis to determine optimal algorithm parameters and generate a final pattern set.

6. The method of any preceding embodiment, further comprising: finding pattern candidates using maximal frequency itemset algorithm (MAFIA); generating a final pattern set under optimal algorithm parameters; and evaluating the final pattern set by performing simulated online analysis; wherein the method is performed by executing programming on at least one computer processor, the programming residing on a non-transitory medium readable by the computer processor.

7. The method of any preceding embodiment, further comprising: pre-processing the data to unify alarm names and exclude crisis alarms; excluding code blue patients with abnormally small number of alarms using a non-homogeneous Poisson Process (NHPP) model; and integrating monitor alarm data with laboratory results.

8. The method of any preceding embodiment, further comprising: transforming the sequences of matching patterns to a fixed-dimension vector; and classifying fixed-dimension vectors with at least one training classifier to predict future clinical events.

9. The method of any preceding embodiment, wherein the fixed-dimension vector transformation comprises:

$$f_i(T) = \frac{1}{\Delta t} \sum_{t=T-\Delta t}^{T} h_i(t)$$

where $h_i(t) =$
$$\begin{cases} 1 & \text{if the } i\text{-th matching pattern is triggered at time } t \\ 0 & \text{if the } i\text{-th matching pattern is not triggered at time } t \end{cases}$$

then the vector $F(T)=N(T), f_1(T), \ldots, f_N(T)]$ is a vector representation of a matching pattern sequence between time $T-\Delta t$ and $T$ where N is the total number of distinctive matching patterns that are deployed.

10. The method of any preceding embodiment, wherein the fixed-dimension vector transformation comprises:

$$f_i(T) = \log\left(1 + \frac{1}{\Delta t}\sum_{t=T-\Delta t}^{T} h_i(t)\right) \times \log\left(\frac{M}{1 + \begin{bmatrix} \text{number of sequences} \\ \text{having at least} \\ \text{one } i\text{-th matching pattern} \\ \text{triggered} \end{bmatrix}}\right)$$

where M is the total number of matching pattern sequences in a training data set.

11. The method of any preceding embodiment, wherein the fixed-dimension vector transformation is a weighted accumulated occurrence representation comprising:

$$f_i(T) = \sum_{t=0}^{T} w(T-t) \times h_i(t)$$

12. A system for monitoring patient data streams, comprising: (a) a processor; and (b) a memory storing instructions executable by the processor; (c) said instructions when executed by the processor performing steps comprising: (i) collecting patient data; (ii) pre-processing the data to unify alarm names and exclude crisis alarms; (iii) excluding code blue patients with abnormally small number of alarms using a non-homogeneous Poisson Process (NHPP) model; (iv) integrating monitor alarms with laboratory results; (v) finding pattern candidates using maximal frequency itemset algorithm (MAFIA); (vi) generating a final matching pattern set under optimal algorithm parameters; (vii) evaluating the final pattern set by performing simulated online analysis; (viii) comparing a clinical data stream of a patient with the identified patterns to identify matching patterns; and (ix) predicting a medical status of the patient based on a sequence of observed matching patterns.

13. The method of any preceding embodiment, wherein when executed said instructions perform steps comprising assessing the performance of the matching patterns using an independent test data set not used in a training phase.

14. The method of any preceding embodiment, wherein when executed said instructions perform steps comprising calculating sensitivity with respect to a prediction window and calculating sensitivity with respect to lead time.

15. The method of any preceding embodiment, further comprising: integrating latest abnormal results of each type of laboratory tests with an array of monitor alarm data within a $T_w$-long window; selecting abnormal laboratory test results from the dataset based on the associated flags as reported by an electronic medical record (EMR) system; using the difference between last two results of a laboratory test before a $T_w$-long window as a laboratory test trigger to be integrated with monitor alarms; creating two extended datasets comprising: a Ab Lab+Alarm dataset comprising an Alarm dataset integrated with abnormal laboratory test results; and a Delta Lab+Alarm dataset, which consists of the Alarm dataset integrated with delta laboratory test results; encoding parametric monitor alarms by discretizing their numeric values using the Class-Attribute Contingency Coefficient (CACC) algorithm; evaluating the patterns by performing offline and simulated online analysis; and performing offline analysis to determine optimal algorithm parameters and generate a final pattern set.

16. The method of any preceding embodiment, wherein the pre-processing comprises excluding "crisis" monitor alarms signaling asystole, ventricular fibrillation, and no breath; and excluding patient data with abnormally small number of monitor alarms.

17. A method for predicting in-hospital code blue events using a term frequency inverse document frequency based kernel.

18. The method of any preceding embodiment, further comprising using a support vector machine (SVM) with term frequency inverse document frequency (TFIDF) based kernel to measure the distance between two sequences of matching patterns.

19. The method and recited in any previous embodiment, further comprising generating pattern sequences are generated for both code blue patients and control patients by applying the identified patterns to the sequence of monitor alarms and laboratory test results.

20. The method of any preceding embodiment, further comprising: for positive examples, training the SVM with six-hour long subsequences immediately prior to the onset of code blue events; and for negative examples, randomly selecting six-hour long subsequences over the whole matching pattern sequence of control patients.

21. The method of any preceding embodiment, further comprising: representing the six-hour long subsequences by TFIDF; and calculating a TFIDF-based kernel that measures the similarity of two 6-hour long subsequences.

22. The method of any preceding embodiment, further comprising evaluating performance of the SVM using 5-fold cross-validation.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method of identifying and predicting patient clinical status changes, the method comprising:
    (a) creating a database of medical data and laboratory data of a pool of healthy and unhealthy patients;
    (b) identifying patterns of temporally occurring clinical events and laboratory results of unhealthy patients with target conditions;
    (c) comparing a clinical data stream of a patient with said identified patterns to identify matching patterns;
    (d) predicting a medical status of the patient based on a sequence of observed matching patterns;
    (e) using a maximal frequent itemsets mining algorithm to find patterns from the integrated dataset;
    (f) generating a final set of patterns by using optimal parameters determined by a 10-fold cross validation of training data;
    (g) filtering out patterns if their false positive rates based on the training data are greater than a user-specified $FPR_{max}$;
    (h) integrating latest abnormal results of each type of laboratory tests with an array of monitor alarm data within a $T_w$-long window;
    (i) selecting abnormal laboratory test results from the dataset based on the associated flags as reported by an electronic medical record (EMR) system;
    (j) using the difference between last two results of a laboratory test before a $T_w$-long window as a laboratory test trigger to be integrated with monitor alarms;
    (k) creating two extended datasets comprising:
        a Ab Lab+Alarm dataset comprising an Alarm dataset integrated with abnormal laboratory test results; and
        a Delta Lab+Alarm dataset comprising the Alarm dataset integrated with delta laboratory test results;
    (l) encoding parametric monitor alarms by discretizing their numeric values using the Class-Attribute Contingency Coefficient(CACC) algorithm;
    (m) evaluating the patterns by performing offline and simulated online analysis; and
    (n) performing offline analysis to determine optimal algorithm parameters and generate a final pattern set.

2. A method of identifying and predicting patient clinical status changes, the method comprising:
    (a) creating a database of medical data and laboratory data of a pool of healthy and unhealthy patients;
    (b) identifying patterns of temporally occurring clinical events and laboratory results of unhealthy patients with target conditions;
    (c) comparing a clinical data stream of a patient with said identified patterns to identify matching patterns;
    (d) predicting a medical status of the patient based on a sequence of observed matching patterns;
    (e) finding pattern candidates using maximal frequency itemset algorithm (MAFIA);
    (f) generating a final pattern set under optimal algorithm parameters;
    (g) evaluating the final pattern set by performing simulated online analysis;
    (h) pre-processing the data to unify alarm names and exclude crisis alarms;
    (i) excluding code blue patients with abnormally small number of alarms using a non-homogeneous Poisson Process (NHPP) model; and
    (j) integrating monitor alarm data with laboratory results.

3. A method of identifying and predicting patient clinical status changes, the method comprising:
    (a) creating a database of medical data and laboratory data of a pool of healthy and unhealthy patients;
    (b) identifying patterns of temporally occurring clinical events and laboratory results of unhealthy patients with target conditions;
    (c) comparing a clinical data stream of a patient with said identified patterns to identify matching patterns;
    (d) predicting a medical status of the patient based on a sequence of observed matching patterns;
    (e) collecting sequences of matching patterns of patients in a pool of healthy and unhealthy patients;
    (f) comparing collected sequences to observed matching pattern sequences of a patient data stream;
    (g) evaluating matching sequences of patterns of the patient data stream;
    (h) transforming said sequences of matching patterns to a fixed-dimension vector; and
    (i) classifying fixed-dimension vectors with at least one training classifier to predict future clinical events.

4. The method as recited in claim 3, wherein said fixed-dimension vector transformation comprises:

$$f_i(T) = \frac{1}{\Delta t} \sum_{t=T-\Delta t}^{T} h_i(t)$$

-continued where $h_i(t) =$
$$\begin{cases} 1 & \text{if the } i\text{-th matching pattern is triggered at time } t \\ 0 & \text{if the } i\text{-th matching pattern is not triggered at time } t \end{cases}$$

then the vector $F(T)=[f_1(T), f_1(T), \ldots, f_N(T)]$ is a vector representation of a matching pattern sequence between time $T-\Delta t$ and $T$ where $N$ is the total number of distinctive matching patterns that are deployed.

5. The method as recited in claim 3, wherein said fixed-dimension vector transformation comprises:

$$f_i(T) = \log\left(1 + \frac{1}{\Delta t}\sum_{t=T-\Delta t}^{T} h_i(t)\right) \times \log\left(\frac{M}{1 + \begin{bmatrix}\text{number of sequences} \\ \text{having at least} \\ \text{one } i\text{-th matching pattern} \\ \text{triggered}\end{bmatrix}}\right)$$

where M is the total number of in a training data set.

6. The method as recited in claim 3, wherein said fixed-dimension vector transformation is a weighted accumulated occurrence representation comprising:

$$f_i(T) = \sum_{t=0}^{T} w(T-t) \times h_i(t).$$

7. A system for monitoring patient data streams, comprising:
(a) a processor; and
(b) a memory storing instructions executable by the processor;
(c) said instructions when executed by the processor performing steps comprising:
(i) collecting patient data;
(ii) pre-processing the data to unify alarm names and exclude crisis alarms;
(iii) excluding code blue patients with abnormally small number of alarms using a non-homogeneous Poisson Process (NHPP) model;
(iv) integrating monitor alarms with laboratory results;
(v) finding pattern candidates using maximal frequency itemset algorithm (MAFIA);
(vi) generating a final matching pattern set under optimal algorithm parameters;
(vii) evaluating the final pattern set by performing simulated online analysis;
(viii) comparing a clinical data stream of a patient with said identified patterns to identify matching patterns; and
(ix) predicting a medical status of the patient based on a sequence of observed matching patterns.

8. The system as recited in claim 7, wherein when executed said instructions perform steps comprising assessing the performance of the matching patterns using an independent test data set not used in a training phase.

9. The system as recited in claim 8, wherein when executed said instructions perform steps comprising calculating sensitivity with respect to a prediction window and calculating sensitivity with respect to lead time.

10. The system as recited in claim 7, wherein when executed said instructions perform steps comprising:
integrating latest abnormal results of each type of laboratory tests with an array of monitor alarm data within a $T_w$-long window;
selecting abnormal laboratory test results from the dataset based on the associated flags as reported by an electronic medical record (EMR) system;
using the difference between last two results of a laboratory test before a $T_w$-long window as a laboratory test trigger to be integrated with monitor alarms;
creating two extended datasets comprising:
a Ab Lab+Alarm dataset comprising an Alarm dataset integrated with abnormal laboratory test results; and
a Delta Lab+Alarm dataset comprising the Alarm dataset integrated with delta laboratory test results;
encoding parametric monitor alarms by discretizing their numeric values using the Class-Attribute Contingency Coefficient(CACC) algorithm;
evaluating the patterns by performing offline and simulated online analysis; and
performing offline analysis to determine optimal algorithm parameters and generate a final pattern set.

11. The system as recited in claim 7, wherein said pre-processing comprises:
excluding "crisis" monitor alarms signaling asystole, ventricular fibrillation, and no breath; and
excluding patient data with abnormally small number of monitor alarms.

12. A method for predicting in-hospital code blue events comprising:
using a support vector machine (SVM) with term frequency inverse document frequency (TFIDF) based kernel to measure the distance between two sequences of matching patterns;
generating pattern sequences are generated for both code blue patients and control patients by applying the identified patterns to the sequence of monitor alarms and laboratory test results;
for positive examples, training the SVM with six-hour long subsequences immediately prior to the onset of code blue events; and
for negative examples, randomly selecting six-hour long subsequences over the whole matching pattern sequence of control patients.

13. The method as recited in claim 12, further comprising:
representing the six-hour long subsequences by TFIDF; and
calculating a TFIDF-based kernel that measures the similarity of two 6-hour long subsequences.

14. The method as recited in claim 13, further comprising evaluating performance of the SVM using 5-fold cross-validation.

15. The as recited in claim 1, further comprising triggering a monitor alarm when an identified pattern matches data points in a patient data stream.

16. The as recited in claim 2, further comprising triggering a monitor alarm when an identified pattern matches data points in a patient data stream.

17. The as recited in claim 3, further comprising triggering a monitor alarm when an identified pattern matches data points in a patient data stream.

18. The as recited in claim 1, further comprising:
collecting sequences of matching patterns of patients in a pool of healthy and unhealthy patients;
comparing collected sequences to observed matching pattern sequences of a patient data stream; and evaluating matching sequences of patterns of the patient data stream.

19. The as recited in claim 2, further comprising:

collecting sequences of matching patterns of patients in a pool of healthy and unhealthy patients;

comparing collected sequences to observed matching pattern sequences of a patient data stream; and evaluating matching sequences of patterns of the patient data stream.

20. The as recited in claim 2, further comprising:

using a maximal frequent itemsets mining algorithm to find patterns from the integrated dataset;

generating a final set of patterns by using optimal parameters determined by a 10-fold cross validation of training data; and filtering out patterns if their false positive rates based on the training data are greater than a user-specified $FPR_{max}$.

21. The as recited in claim 3, further comprising:

using a maximal frequent itemsets mining algorithm to find patterns from the integrated dataset;

generating a final set of patterns by using optimal parameters determined by a 10-fold cross validation of training data; and filtering out patterns if their false positive rates based on the training data are greater than a user-specified $FPR_{max}$.

22. The as recited in claim 1, further comprising:

finding pattern candidates using maximal frequency itemset algorithm (MAFIA);

generating a final pattern set under optimal algorithm parameters; and evaluating the final pattern set by performing simulated online analysis.

23. The as recited in claim 3, further comprising:

finding pattern candidates using maximal frequency itemset algorithm (MAFIA);

generating a final pattern set under optimal algorithm parameters; and evaluating the final pattern set by performing simulated online analysis.

* * * * *